(12) United States Patent
Mangelberger et al.

(10) Patent No.: US 10,485,405 B2
(45) Date of Patent: Nov. 26, 2019

(54) COUPLING DEVICE FOR RELEASABLE CONNECTION OF A MEDICAL OR DENTAL HANDPIECE TO A DRIVE UNIT OR TO A SUPPLY TUBING

(71) Applicant: W&H Dentalwerk Bürmoos GmbH, Bürmoos (AT)

(72) Inventors: Michael Mangelberger, St. Georgen (AT); Christian Pruckner, Vienna (AT)

(73) Assignee: W&H Dentalwerk Bürmoos GmbH, Bürmoos (AT)

(*) Notice: Subject to any disclaimer, the term of this patent is extended or adjusted under 35 U.S.C. 154(b) by 50 days.

(21) Appl. No.: 15/384,707

(22) Filed: Dec. 20, 2016

(65) Prior Publication Data

US 2017/0100015 A1    Apr. 13, 2017

Related U.S. Application Data

(63) Continuation of application No. PCT/EP2015/065530, filed on Jul. 8, 2015.

(30) Foreign Application Priority Data

Jul. 8, 2014    (EP) .................................... 14176040

(51) Int. Cl.
*A61B 1/00*    (2006.01)
*A61B 90/98*    (2016.01)
(Continued)

(52) U.S. Cl.
CPC ...... *A61B 1/00124* (2013.01); *A61B 1/00016* (2013.01); *A61B 1/00126* (2013.01);
(Continued)

(58) Field of Classification Search
CPC ............ A61B 1/00124; A61B 1/00016; A61B 1/00126; A61B 1/00128;
(Continued)

(56) References Cited

U.S. PATENT DOCUMENTS 4,720,266 A * 1/1988 Leonard .................. A61C 1/18
                                                                 433/126
5,501,596 A * 3/1996 Bailey ..................... A61C 17/20
                                                                 433/119
(Continued)

FOREIGN PATENT DOCUMENTS

AT          389633        1/1990
DE     102006051511       5/2008
(Continued)

OTHER PUBLICATIONS

International Search Report for PCT/EP2015/065530 (dated Sep. 4, 2015).

*Primary Examiner* — Cris L. Rodriguez
*Assistant Examiner* — Hao D Mai
(74) *Attorney, Agent, or Firm* — Klarquist Sparkman, LLP

(57) ABSTRACT

A coupling device for releasably connecting a handpiece to another component. One of a first coupling element and a second coupling element, is designed as a coupling cavity, into which a coupling protrusion on the other coupling element can be inserted. A positioning element is disposed on the first coupling element or the second coupling element and can be inserted into a first recess on the other coupling element to position the two coupling elements in a defined angular position about their common axis. A light source disposed in a second recess on the first or second coupling element can be coupled to an optical fiber on the other coupling element. A transfer element disposed on the first or second coupling element and inserted into a third recess on the other coupling element is configured to transfer data, signals and/or energy between the first and second coupling elements.

20 Claims, 2 Drawing Sheets

(51) Int. Cl.
*A61C 1/00* (2006.01)
*A61C 1/08* (2006.01)
*A61C 1/12* (2006.01)

(52) U.S. Cl.
CPC .......... *A61B 1/00128* (2013.01); *A61B 90/98* (2016.02); *A61C 1/0015* (2013.01); *A61C 1/0061* (2013.01); *A61C 1/088* (2013.01); *A61C 1/12* (2013.01); *A61B 2562/226* (2013.01); *A61C 2204/005* (2013.01)

(58) Field of Classification Search
CPC .... A61B 2017/00482; A61B 2562/226; A61C 2204/005
See application file for complete search history.

(56) References Cited

U.S. PATENT DOCUMENTS

| | | | | |
|---|---|---|---|---|
| 6,159,004 | A * | 12/2000 | Rosenstatter | A61C 1/088 433/126 |
| 8,853,895 | B2 * | 10/2014 | Duesing | A61C 1/0061 310/50 |
| 2001/0031442 | A1 * | 10/2001 | Mosimann | A61C 1/18 433/126 |
| 2004/0166464 | A1 * | 8/2004 | Schneider | A61C 1/08 433/29 |
| 2010/0221676 | A1 * | 9/2010 | Kuhn | A61C 1/088 433/29 |
| 2011/0207353 | A1 * | 8/2011 | Sauter | A61B 17/1626 439/191 |
| 2012/0129124 | A1 * | 5/2012 | Lancieux | A61C 1/088 433/29 |
| 2014/0212833 | A1 * | 7/2014 | Mangelberger | A61C 1/0015 433/80 |

FOREIGN PATENT DOCUMENTS

| | | |
|---|---|---|
| EP | 1321108 | 6/2003 |
| EP | 2581061 | 4/2013 |

* cited by examiner

COUPLING DEVICE FOR RELEASABLE CONNECTION OF A MEDICAL OR DENTAL HANDPIECE TO A DRIVE UNIT OR TO A SUPPLY TUBING

CROSS REFERENCE TO RELATED APPLICATION

This application is a U.S. bypass continuation application of International Application No. PCT/EP2015/065530, filed Jul. 8, 2015, which in turn claims priority from pending European Patent Application No. EP 14176040.5, filed Jul. 8, 2014, which are incorporated herein by reference.

BACKGROUND

Field

The present invention relates to a coupling device for releasable connection of a medical or dental handpiece to a drive unit or to a supply tubing.

Description of Prior Art

Such coupling devices are used for transfer of signals, data, energy, light, a drive movement and/or a working medium, in particular a fluid between two medical or dental devices. One of the devices here is preferably designed as a dental handpiece or contra-angle handpiece for connection of medical, in particular dental tools, which preferably serve to treat hard or soft tissue or for introducing implants. The term "handpieces" is understood to include straight, curved or gun-shaped handpieces as well as parts of handpieces, adapters, diagnostic devices and light probes. The handpieces or contra-angle handpieces are preferably connected to a second coupling part, which is preferably disposed on a medical or dental drive unit or on a supply tubing through the coupling device, in particular through a first coupling part of the coupling device, in order to drive the medical tools by an electric motor disposed in the drive unit. During operation of the medical tools, these tools as well as the handpieces or contra-angle handpieces are to be supplied with working media, for example, spray air and/or spray water for cooling or with electric energy. These media are supplied by a dental unit in particular and sent to the drive unit or to the handpiece or contra-angle handpiece through a supply line via the coupling device.

For transfer of data and energy, the coupling devices often have electric contacts or induction coils. The coils here are preferably disposed in the interior of the coupling parts of the coupling device, in particular in a sleeve wall, in a coupling journal or behind a coupling journal base of the coupling device.

Such a coupling device having a first and second coupling element for supplying the handpiece with a drive movement, working media and with data and energy is known in particular from EP 2 581 061 A1: a positioning element is disposed on one of the two coupling elements of the coupling device in order to position both coupling elements in a defined angular position to one another. A memory unit is disposed in the positioning element for saving instrument-related data. The transfer of data from the memory unit to the other coupling element preferably takes place here via a hardwired system and a second electric contact in a recess on the other coupling element. The positioning element and the recess additionally each have an induction coil for wireless transfer of energy, preferably for a light source in the handpiece.

One disadvantage of this design of the coupling device has proven to be the transfer of instrument-related data from the memory unit by an electric contact and the transfer of energy for an electric component by an induction coil in the positioning element of the coupling device.

In a simultaneous transfer of energy and data, all the components situated in the area of the electric contacts and the induction coils must be made of electrically non-conductive materials in order not to endanger the transfer of energy and data through the opposing fields generated in the electrically conductive components. With the arrangement of an electric contact, an electric line and an induction coil in the positioning element, such as that known in the state of the art, there is thus the risk that opposing electric or magnetic fields, which threaten the transfer of energy and data between the two coupling elements, are created through the electrically conductive components.

Shielding of the electrically conductive components for the transfer of energy and data has also proven to be a disadvantage based on increased cost for the expensive shielding as well as based on the associated greater space required for the data and energy transfer.

The limited transfer of data and energy is another disadvantage of the embodiment known from the state of the art. The arrangement of the electric contacts and the induction coils in the positioning element and the recess does make it possible to design existing coupling devices, in particular dental handpieces for sending and receiving data and energy due to the standardized design size of the positioning element, but for reasons of space, a transfer of energy and data is possible only to a limited extent. In particular, various data and signals, for example, information about the length of a root canal, sensor data or identification signals can be transferred only serially from the one coupling element to the other coupling element of the coupling device by the known coupling device.

SUMMARY

Based on the foregoing it is an object to create a coupling device for a releasable connection of a medical or dental handpiece to a drive unit or to a supply tubing, which will make it possible in particular to transfer signals, data and/or energy reliably from the one coupling element to the other coupling element of the coupling device for a plurality of electronic components.

According to one embodiment of a coupling device for releasable connection of a medical or dental handpiece to a drive unit or to a supply tubing for transfer of signals, data and/or energy, a drive movement, a working medium and/or light between the handpiece and the drive unit or the supply tubing, the coupling device comprises a first and a second coupling element, wherein one of the two coupling elements is designed as a coupling cavity, into which a coupling protrusion on the other coupling element can be inserted, a positioning element disposed on the first or second coupling element, insertable into a first recess on the other coupling element in order to position the two coupling elements in a defined angular position about their common axis to one another, at least one light source, which is disposed in a second recess on the first or second coupling element and can be coupled to a light guide on the other coupling element as well as at least one transfer element disposed on the first or second coupling element, insertable into a third recess on the other coupling element to reliably transfer data, signals and/or energy between the first and second coupling elements.

According to a first embodiment of the coupling device, one of the two elements, i.e., the positioning element or the first recess, comprises a memory unit for storage of data, preferably data related to the handpiece, and the other one of the two elements has a reader unit, so that data from the memory unit of the one coupling element can be transferred by means of the reader unit to the other coupling element of the coupling device.

For hardwired and/or wireless transmission of data, signals or energy from the one coupling element to the other coupling element, the positioning element and the first recess as well as the transmission element and the third recess preferably have electric contacts and/or induction coils. The electric contacts are preferably spring-mounted, so that they can preferably be displaced parallel to the axis or in the radial direction to the axis of the coupling device. Wireless transmission of data and signals is not limited to induction coils, but instead may also take place optically by means of infrared light, for example.

According to a second embodiment of the coupling device, one of the two elements, the transfer element or the third recess comprises at least one sensor, so that operating parameters of the one coupling element, in particular of the handpiece or the drive unit can be detected by the sensor and transferred to the other coupling element of the coupling device. The at least one sensor is designed in particular to detect values such as temperature, moisture, pressure, sound or brightness in the other coupling element, in particular in the handpiece or the drive unit.

According to a third embodiment of the coupling device, one of the two elements, the transfer element or the third recess, comprises a camera, so that image data in particular of a tissue to be treated can be recorded by the camera and transferred from the one coupling element to the other coupling element of the coupling device. The image data can preferably allow conclusions regarding the physical properties of the tissue to be treated.

According to all the preceding embodiments, the positioning element and/or the transfer element is/are preferably spring-mounted, so that it/they can be displaced preferably in parallel with the axis of the coupling device. In addition, the positioning element and/or the transfer element is/are preferably designed to be releasable from the coupling element of the coupling device. The coupling element therefore preferably comprises a screw connection, a plug connection and/or a snap connection.

To reliably transfer the data, signals and/or energy from the one coupling element to the other coupling element, the positioning element or the first recess, the second recess for receiving the light source and the transfer element or the third recess on the first or second coupling element is/are preferably disposed in front of the base surface from which the coupling protrusion extends.

In addition, according to all the preceding embodiments, the positioning element or the first recess and the second recess for the light source are disposed on the first or second coupling element in the opposite radial direction from the common axis of the two coupling elements. The transfer element and the third recess are preferably positioned on the first and second coupling elements at an angle of preferably 55 degrees offset from the radial direction of the second recess for the light source.

In addition, the positioning element, the transfer element as well as the second recess for the light source is/are disposed on the first and second coupling elements, preferably at the same radial distance.

The present coupling device has the following advantages:

The coupling device according to the invention permits signals, data and/or energy to be reliably transferred from the one coupling element to the other coupling element of the coupling device. The arrangement of the positioning element and the transmission element, in particular of the electric contacts and the induction coils for hardwired and wireless transmission of energy and data, at a distance from one another on the first and second coupling element of the coupling device prevents the creation of opposing fields during the transmission of energy and data. In addition, no further shielding of the electric contacts and induction coils is necessary.

Another advantage of the invention is achieved with the arrangement of the electric contacts, the induction coils, the sensors and the camera for transmission of signals, data and/or energy outside of the metal components of the coupling device, in particular outside of the sleeve for the coupling cavity and outside of the coupling protrusion in the transfer element and/or in the positioning element of the coupling device. In this way these components are accessible from several sides and can be inserted into the other respective coupling element, in particular into the handpiece, the drive unit or into the supply tubing, so that signals and data in particular can be detected directly in the respective other coupling element.

In addition, the coupling device makes it possible to transfer reliably the signals, data and/or energy from a plurality of electronic components in the handpiece, the drive unit and/or the supply tubing at the same time and/or in parallel from the one coupling element to the other coupling element of the coupling device.

Another advantage of the invention is the compatibility of the coupling device, in particular of the coupling elements, with existing coupling elements, in particular with existing dental handpieces. Due to the fact that the transfer element for sending and/or receiving signals, data and/or energy is preferably disposed on the coupling element of the handpiece, it is possible to couple existing handpieces to the respective other coupling element of the coupling device according to the invention. The drive units are thus still compatible without any functional restriction with the existing medical handpieces and/or their coupling elements.

Within the scope of the invention it is of course self-evident that the coupling device described above is not limited to use with a medical or dental handpiece and a drive unit. The coupling device may instead be used for releasable connection of two medical or dental devices. At least one of the medical or dental devices is preferably designed as a cleaning and/or care device, as a drive unit, as a supply tubing, as a diagnostic device or as a handpiece with a drive device for a tool.

These and other embodiments will be described below with reference to the following drawings.

DETAILED DESCRIPTION

Figure 1:
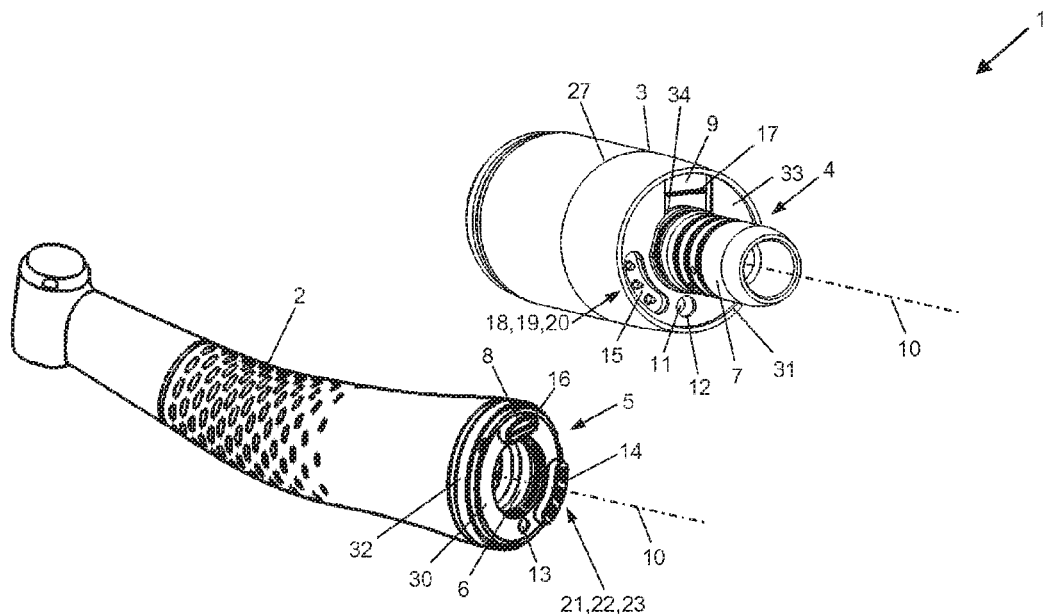
FIG. 1 shows a first embodiment of the coupling device with a first coupling element on a drive unit and a second coupling element on a medical or dental handpiece.

FIG. 1 shows a first embodiment of the coupling device 1 with a first coupling element 4 on a drive unit 3 and a second coupling element 5 on a medical, in particular dental handpiece 2. For releasable connection of the handpiece 2 to the drive unit 3 and for transfer of a drive movement as well as a working medium, in particular a fluid, the first coupling element 4 has a coupling protrusion 7, which can be inserted into a coupling cavity 6 on the second coupling element 5 up to a stop face 34. The stop face 34 is preferably disposed on the coupling protrusion 7. The length of the coupling protrusion 7, measured from the stop face 34, is preferably less than 23 millimeters, in particular 21.60 millimeters, in order to be accommodated in the coupling cavity 6, which is at least 23 millimeters deep. To align a light source 11 of the drive unit 3, in particular a light-emitting diode, which is disposed in a recess 12 to a corresponding optical fiber 13 on the medical handpiece 2, the coupling device 1, in particular the second coupling element 5 with the coupling cavity 6, has a positioning element 8, which can be inserted into a first recess 9 on the first coupling element 4. In this way, both coupling elements 4, 5 can be positioned in a defined angular position to one another about their common axis 10. The positioning element 8 preferably extends in the opposite direction from the coupling cavity 6 on the second coupling element 5 and is designed in particular as a nose, a protrusion or an extension. In addition, the positioning element 8 is preferably spring-mounted, so that it is preferably displaceable in parallel with the longitudinal or rotational axis 10 of the coupling device 1.

For automatic detection of the medical handpiece 2 that can be connected to the drive unit 3, the positioning element 8 preferably has a memory unit 16 for storage of data, preferably data relating to the handpiece. A reader unit 17 in the first recess 9 is provided to read out the data from the memory unit 16 and transferred to the coupling element 4 of the drive unit 3. The transfer preferably takes place by two induction coils, one coil being disposed in the positioning element 8 and one coil being disposed in the recess 9. Data may thus also be transferred from the drive unit 3 to the memory unit 16 of the handpiece 2. Both the memory unit 16 and the respective induction coil are preferably disposed outside of the handpiece 2 in the positioning element 8, so that they are freely accessible from a plurality of sides for the other coupling element 4, in particular for reader unit 17. In addition, the positioning element 8 with the memory unit 16 is preferably designed to be releasable from the coupling element 5, so that it is replaceable.

In this embodiment the reader unit 17 is preferably disposed in front of a base surface 27 from which the coupling protrusion 7 extends. This ensures reliable data transmission between the memory unit 16 and the reader unit 17. Electrically conductive components which would endanger the data transfer due to electric or opposing magnetic fields, such as the base surface 27 of the coupling protrusion, are not disposed between the memory unit 16 and the reader unit 17.

For transfer of signals, data and/or energy between the two coupling elements 4, 5, the second coupling element 5 comprises a transfer element 14 which can be introduced into a third recess 15 on the first coupling element 4. Like the positioning element 8, the transfer element 14 preferably extends away from the second coupling element 5, in particular from an annular end face 30, parallel to the axis 10 in the opposition direction from the coupling cavity 6. In addition, the transfer element 14 preferably extends in a radial direction around the axis 10 of the coupling device 1 and therefore has a cross section in the form of a segment of a circle. Like the positioning element 8, the transfer element 14 may also be designed to be spring-loaded, in particular displaceable and releasable, relative to the second coupling element 5. The overhang of the two elements 8, 14 from the stop face 34 amounts in particular to between 1.50 and 2.30 millimeters, preferably 2.25 millimeters in order to be insertable into the recesss 9, 15, which are designed to be at least 2.50 millimeters deep.

For hardwired transfer of the data, signals and/or energy, the transfer element 14, which also has the shape of a nose, a protrusion or a projection, as well as the third recess 15 preferably have electric contacts 18, 19, 20; 21, 22, 23. In this first embodiment, the transfer element 14 as well as the recess 15 each have three electric contacts 18, 19, 20; 21, 22, 23. Preferably, two of the electric contacts 18, 19 and 21, 22 respectively, serve to transfer electrical energy. The additional electric contacts 20, 23 preferably serve to transfer electric signals in particular from root canal positioning signals. The electric contacts 18, 19, 20; 21, 22, 23 are preferably spring-mounted, so that they are preferably displaceable in a radial direction to the axis 10 of the coupling device 1. In particular the electric contacts 18, 19, 20 of the first coupling element 4 are designed as contact pins, which can be inserted into electric contacts 21, 22, 23 of the second coupling element 5 having straps that are spring-mounted in the radial direction. Alternatively, the electric contacts 18, 19, 20; 21, 22, 23 may also be mounted displaceably parallel to the axis 10.

To protect the signal, data and/or energy transfer as well as the transfer of light between the first coupling element 4 and the second coupling element 5 from external influences, one of the two coupling elements 4, 5, in particular the first coupling element 4, comprises an annular protrusion 31. The protrusion 31 extends in the axial direction from an annular end face 33 of the first coupling element 4. In a coupled state of the two coupling elements 4, 5, the annular protrusion 31 thus surrounds at least partially a coupling protrusion 7, the coupling cavity 6, the positioning element 8, the light source 11, the transfer element 14 as well as an external lateral surface 32 of the second coupling element 5.

Figure 2:
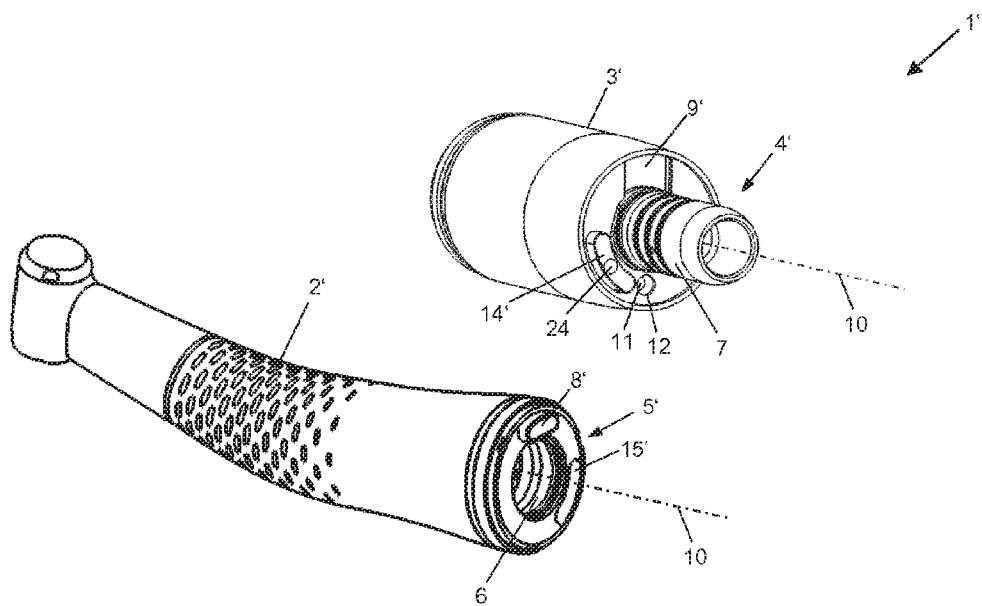
FIG. 2 shows a second embodiment of the coupling device for transfer of signals, data and/or energy, a drive movement and a working medium between the handpiece and the drive unit.

FIG. 2 shows a second embodiment of the coupling device 1' having a coupling protrusion 7 on a first coupling element 4' and a coupling cavity 6 on a second coupling element 5'. The transfer element 14' here is disposed on the first coupling element 4' of the drive unit 3' and the third recess 15' is disposed on the second coupling element 5' of the handpiece 2'. The transfer element 14' extends parallel to the coupling protrusion 7. In order for the two coupling elements 4', 5' to again be positioned in a defined angular position relative to one another about their common axis 10, the handpiece 2' comprises a positioning element 8', which can be inserted into a recess 9' on the drive unit 3'. In this embodiment, the second recess 12 for accommodating the light source 11 is again disposed on the drive unit 3' in the opposite radial direction from the common axis 10 to the recess 9' for the positioning element 8'.

To detect operating parameters of the second coupling element 5', in particular of the handpiece 2', and to transfer them to the first coupling element 4' of the coupling device 1', in particular to the drive unit 3', in this embodiment, the transfer element 14' comprises at least one sensor 24. The sensor 24 is preferably disposed outside of the drive unit 3' in the transfer element 14', so that the latter is freely accessible for the handpiece 2' from a plurality of sides. The sensor 24 is preferably designed to detect temperatures, moisture, pressure, sound or brightness in the second coupling element 5', in particular in the handpiece 2'. In addition, the at least one sensor 24 is designed in particular to transfer the measured values to a control unit of the drive unit 3' by wireless or hardwired transmission. Depending on the operating parameters detected, working media such as light, water, air or spray for cooling the handpiece 2' may be supplied automatically to the medical handpiece 2', which is connected to a dental unit by means of a supply tubing.

Figure 3:
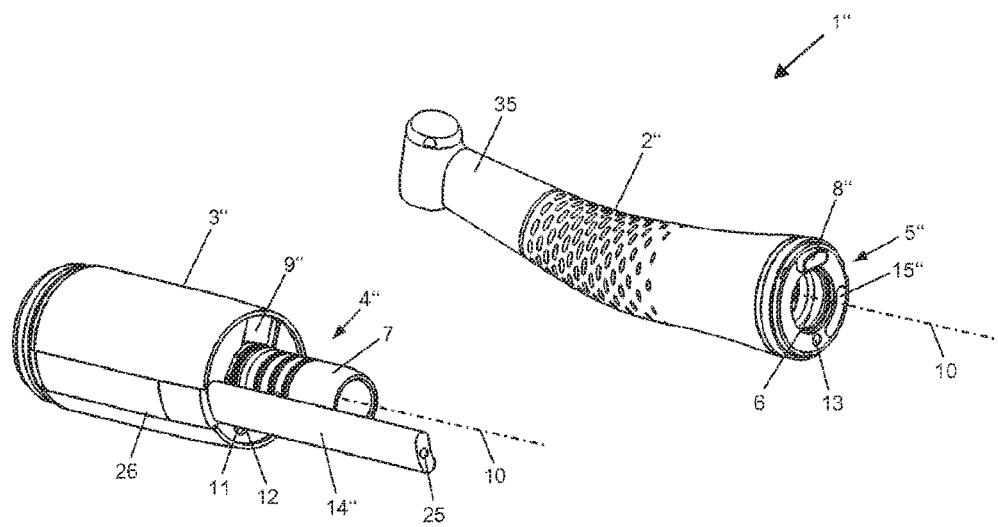
FIG. 3 shows a third embodiment of the coupling device.

FIG. 3 shows a third embodiment of the coupling device 1" with a first and second coupling element 4", 5". As in the preceding embodiments, the first coupling element 4" on the drive unit 3" has a coupling protrusion 7 that can be inserted into a coupling cavity 6 on the second coupling element 5" of the medical handpiece 2". In this embodiment, as in FIG. 2, both the positioning element 8" and the recess 15" for receiving a transfer element 14" are disposed on the medical handpiece 2". In addition to the positioning element 8" and the recess 15", this second coupling element 5" has a recess for an optical fiber 13. The first recess 9" for receiving the positioning element 8", the second recess 12 for the light source 11 and the transfer element 14" are provided on the drive unit 3".

To record image data, in particular of tissue to be treated, and to transfer said image data from the second coupling element 5" of the medical handpiece 2" to the first coupling element 4" of the drive unit 3", the transfer element 14" of the first coupling device 4" has a camera 25. The camera 25 here is positioned on a front end face of the transfer element 14".

In order for the image data to be detectable directly in the area of the treatment tool that can be coupled to the medical handpiece 2", the recess 15" preferably extends from the coupling element 5" into a neck region 35 of the handpiece 2", which connects a head piece having a tool receptacle to the handle piece of the handpiece 2". The recess 15" here is preferably formed by a guide tube. Preferably a lens system is provided on the head end of the medical handpiece 2" which sends image data from the tissue to be treated to the camera 25. Alternatively, an imaging guide may also be disposed in the recess 15".

The transfer element 14" together with the camera 25 is preferably designed to be releasable from the coupling element 4", in particular releasable from the drive unit 3". To do so, the coupling device 1" preferably has a plug and/or snap connection 26 which is formed by a groove extending in the axial direction from a first end of the drive unit 3" to the first coupling element 4". In addition, the transfer element 14" preferably extends parallel to the axis 10 and to the coupling protrusion 7.

Image data detected can be transferred from the camera 25 to a control unit of the drive unit 3", in particular to a dental unit having a display, preferably by a hardwired connection. To do so, the transfer element 14" preferably comprises a plurality of electric lines, which extend from the camera 25 to a rear end of the transfer element 14" or directly to the dental unit.

Figure 4A:
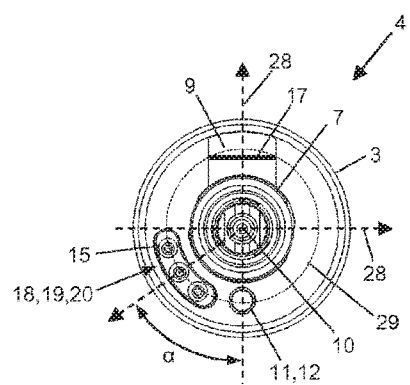
FIGS. 4A to 4C show the embodiments of the first coupling element of the coupling device from FIGS. 1 to 3 in a view from above.
Figure 4B:
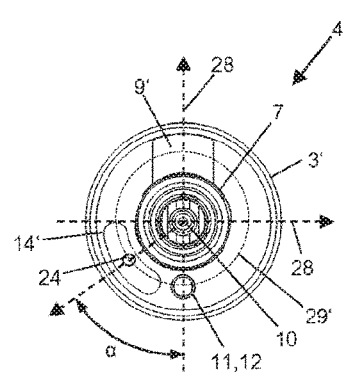
Figure 4C:
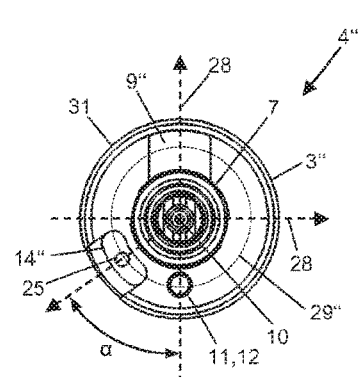

FIGS. 4A to 4C show the embodiments of the first coupling element 4, 4', 4" of the coupling device 1, 1', 1" from FIGS. 1 to 3 in a view from above.

FIG. 4A shows the first embodiment of the first coupling element 4 with the coupling protrusion 7 which is disposed on the drive unit 3. The recess 12 for the light source 11 as well as the recess 15 having electric contacts 18, 19, 20 for receiving the transfer element are preferably disposed at the same radial distance 29 from the common axis 10 on the coupling element 4. In addition, the first recess 9 for the positioning element with the reader unit 17 and the second recess 12 for the light source 11 are disposed on the coupling element 4 in the opposite radial direction 26 from the common axis 10. The recess 15 for the transfer element is positioned on the coupling element 4, so that it is offset from the radial direction of the second recess 12 for the light source 11 by an angle α of preferably 55 degrees.

FIG. 4B shows the second embodiment of the first coupling element 4' with the coupling protrusion 7 on the drive unit 3'. Again in this embodiment, the recess 12 for the light source 11 as well as the transfer element 14' with the at least one sensor 24 are disposed on the coupling element 4' at the same radial distance 29' from the common axis 10. The distance is preferably 7.50 millimeters. In the radial direction 28 to the common axis 10, the first recess 9' for the positioning element and the second recess 12 for the light source 11 are also positioned on the coupling element 4', likewise in the opposite direction. The transfer element 14', which is offset by the angle α relative to the radial direction 28 of the second recess 12 on the coupling element 4', extends preferably by an angle of 70 degrees and thus has a cross section in the form of a segment of a circle.

In the embodiment of the first coupling element 4" with the coupling protrusion 7 on the drive unit 3", as shown in FIG. 4C, the transfer element 14" has a camera 25. The camera 25 and the transfer element 14" are offset from the radial direction 28 of the second recess 12 for the light source 11 by an angle α of preferably 55 degrees, as shown in the previous embodiments, and at the same radial distance 29" from the common axis 10, such as the recess 12 on the coupling element 4". The recess 9" for the positioning element extends here in the radial direction 28 from the coupling journal 7 to the annular protrusion 31.

The present invention is not limited to the embodiments described here but instead includes all embodiments that employ or include the basic function principle of the invention. In addition, all the features of all the embodiments described and depicted here can be combined with one another.

What is claimed is:

1. A coupling device for releasable connection of a medical or dental handpiece to a drive unit or to a supply tubing for transferring signals, data, a drive movement, a working medium and/or light between the handpiece and the drive unit or the supply tubing, the coupling device comprising:

a first coupling element and second coupling element, wherein one of the first coupling element and the second coupling element comprises a coupling cavity and the other of the first coupling element and the second coupling element comprises a coupling protrusion which can be inserted into the coupling cavity, a positioning element which is disposed on the first coupling element or the second coupling element and a first recess on the other of the first coupling element or the second coupling element and dimensioned to receive the positioning element in order to position the first and second coupling elements in a defined angular position about a common axis relative to one another, at least one light source which is disposed in a second recess on the first coupling element or the second coupling element and an optical fiber disposed on the other of the first coupling element or the second coupling element and coupleable to the light source, and
at least one transfer element which is disposed on the first coupling element or the second coupling element and a third recess disposed on the other of the first coupling element or the second coupling element and shaped to receive the transfer element, the transfer element and third recess being configured to transfer data and/or signals between the first and second coupling elements,
wherein when viewed along the common axis of the first and second coupling elements, the transfer element and the third recess are separated from the positioning element and the first recess, respectively, and
wherein when viewed along the common axis of the first and second coupling elements, the transfer element and the third recess are disposed between the positioning element or the first recess and the light source or the second recess or the optical fiber.

2. The coupling device according to claim 1, wherein one of the positioning element and the first recess comprises a memory unit for storing data and the other of the positioning element and the first recess comprises a reader unit, and wherein data can be transferred from the memory unit of the one coupling element to the other coupling element via the reader unit.

3. The coupling device according to claim 1, wherein the positioning element and the first recess comprise electric contacts and/or induction coils for hardwired transfer or wireless transfer, respectively, of data and/or signals between the first and second coupling dements.

4. The coupling device according to claim 1, wherein the transfer element and the third recess comprise electric contacts and/or induction coils for hardwired transfer or wireless transfer, respectively, of data and/or signals between the first and second coupling elements.

5. The coupling device according to claim 4, wherein the electric contacts are spring-mounted, the electric contacts being displaceable in parallel with a longitudinal axis of the coupling device or in a radial direction transverse to the longitudinal axis of the coupling device.

6. The coupling device according to claim 1, wherein one of the transfer element and the third recess comprises at least one sensor, and wherein operating parameters of the first or second coupling element, of the handpiece and/or of the drive unit can be detected by the sensor and communicated through to the other of the first or second coupling element.

7. The coupling device according to claim 1, wherein one of the transfer element and the third recess comprises a camera so that image data can be recorded by the camera and can be transferred from one of the first or second coupling element to the other of the first or second coupling element.

8. The coupling device according to claim 1, wherein at least one of the positioning element and the transfer element is spring-mounted and is displaceable relative to a longitudinal axis of the coupling device.

9. The coupling device according to claim 1, wherein at least one of the positioning element and the transfer element is designed to be releasable from the respective first or second coupling element.

10. The coupling device according to claim 1, further comprising a screw connection, a plug connection and/or a snap connection for releasably receiving at least one of the positioning element and the transfer element.

11. The coupling device according to claim 1, wherein the first coupling element or the second coupling element comprises the coupling protrusion and a base surface from which the coupling protrusion extends, wherein at least one of the positioning element or the first recess, or the second recess, or the transfer element or the third recess is positioned between the base surface and a free end of the coupling protrusion.

12. The coupling device according to claim 1, wherein the positioning element or the first recess, and the second recess for the light source, are disposed on one of the first or second coupling element approximately radially opposite from each other relative to the common axis.

13. The coupling device according to claim 1, wherein at least one of the transfer element and the third recess is circumferentially separated from the second recess by a predetermined angle.

14. The coupling device according to claim 1, wherein the positioning element, the transfer element and the second recess for the light source are disposed on the first and second coupling elements at a same radial distance from the common axis of the first and second coupling elements.

15. A treatment device comprising a first medical or dental device coupleable with a second medical or dental device by a coupling device, the coupling device comprising:
a first coupling element and a second coupling element, wherein one of the first coupling element and the second coupling element comprises a coupling cavity and the other of the first coupling element and the second coupling element comprises a coupling protrusion which can be inserted into the coupling cavity,
a positioning element disposed on the first coupling element or the second coupling element and a first recess on the other of the first coupling element or the second coupling element and dimensioned to receive the positioning element in order to position the first and second coupling elements in a defined angular position about a common axis relative to one another,
at least one light source disposed in a second recess on the first coupling element or the second coupling element and an optical fiber disposed on the other of the first coupling element or the second coupling element and coupleable to the light source, and
at least one transfer element disposed on the first coupling element or the second coupling element and a third recess disposed on the other of the first coupling element or the second coupling element and shaped to receive the transfer element, the transfer element and third recess being configured to transfer data and/or signals between the first and second coupling elements and in turn between the first and second medical or dental devices coupleable by the first and second coupling elements,
wherein when viewed along the common axis of the first and second coupling elements, the transfer element and the third recess are separated from the positioning element and the first recess, respectively, and
wherein when viewed along the common axis of the first and second coupling elements, the transfer element and the third recess are disposed between the positioning element or the first recess and the light source or the second recess or the optical fiber.

16. The treatment device of claim 15, wherein the first and second medical or dental devices comprise two of a handpiece, a drive unit, a supply tubing, a cleaning or care device, or a diagnostic device.

17. A coupling device for coupling first and second components of a medical or dental system together, the coupling device extending along a longitudinal axis and comprising:

a first coupling element connected to the first component and a second coupling element connected to the second component, wherein one of the first coupling dement and the second coupling element comprises a coupling cavity and the other of the first coupling element and the second coupling element comprises a coupling protrusion which can be inserted into the coupling cavity, and wherein each of the coupling cavity and the coupling protrusion is surrounded by an annular end face, a positioning element disposed on the annular end face of the first coupling element or the second coupling element and a first recess on the annular end face of the other of the first coupling element or the second coupling element and dimensioned to receive the positioning element to position the first and second coupling elements in a defined angular position about a common axis relative to one another, at least one light source disposed in a second recess of the annular end face of the first coupling element or the second coupling dement and an optical fiber disposed on the annular end face of the other of the first coupling element or the second coupling element and coupleable to the light source, and at least one transfer element disposed on the annular end face of the first coupling element or the second coupling element and a third recess disposed on the annular end face of the other of the first or second coupling elements and shaped to receive the transfer element, the transfer element and third recess being configured to transfer data and/or signals between the first and second coupling dements and in turn between the first and second components, wherein when the annular end faces are viewed along the common axis of the first and second coupling elements, the transfer element and the third recess are separated by a segment of the annular end faces from the positioning element and the first recess, respectively, and wherein when the annular end faces are viewed along the common axis of the first and second coupling elements, the transfer element and the third recess are disposed between the positioning element or he first recess, and the light source, the second recess or the optical fiber, in a circumferential direction around the common axis.

18. The coupling device according to claim 17, wherein the transfer element and the third recess comprise electric contacts for hardwired transfer or induction coils for wireless transfer, respectively, of data and/or signals between the first and second coupling elements.

19. The coupling device according to claim 17, wherein the first recess and the third recess are arranged on the first coupling element and the positioning element and the at least one transfer element are arranged on the second coupling element.

20. The coupling device according to claim 19, wherein one of the first and second components of the medical or dental system comprises a handpiece having the second coupling element.

* * * * *

UNITED STATES PATENT AND TRADEMARK OFFICE
CERTIFICATE OF CORRECTION

PATENT NO. : 10,485,405 B2
APPLICATION NO. : 15/384707
DATED : November 26, 2019
INVENTOR(S) : Mangelberger et al.

It is certified that error appears in the above-identified patent and that said Letters Patent is hereby corrected as shown below:

In the Claims

Column 11, Line 3, "coupling dement" should read --coupling element--.

Column 11, Line 19, "coupling dement" should read --coupling element--.

Column 12, Line 2, "coupling dements" should read --coupling elements--.

Column 12, Line 13, "or he first" should read --or the first--.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*